United States Patent [19]

Jönsson et al.

[11] Patent Number: 5,770,064
[45] Date of Patent: Jun. 23, 1998

[54] COMBINED HOLDER AND CONNECTOR FOR A DIALYSER

[75] Inventors: Jörgen Jönsson, Sjöbo; Daniel Höglund, Stockholm, both of Sweden

[73] Assignee: Gambro AB, Sweden

[21] Appl. No.: 659,140

[22] Filed: Jun. 4, 1996

[30] Foreign Application Priority Data

Jun. 6, 1995 [SE] Sweden .................................. 9502048

[51] Int. Cl.$^6$ ............................ B01D 61/30; B01D 65/00
[52] U.S. Cl. ........................... 210/232; 210/239; 210/240; 210/646
[58] Field of Search .................................... 210/232, 237, 210/239, 240, 646

[56] References Cited

U.S. PATENT DOCUMENTS

D. 251,440  3/1979  Inoue ........................................ D24/31
4,191,351   3/1980  Goyne .
5,275,724   1/1994  Bucchianeri et al. ................... 210/232

FOREIGN PATENT DOCUMENTS 3642671  6/1988  Germany .

OTHER PUBLICATIONS

English translation of German Patent No. DE 36 42 671.

Primary Examiner—John Kim
Attorney, Agent, or Firm—Lerner, David, Littenberg, Krumholz & Mentlik

[57] ABSTRACT

A combined holder and connector for a dialysis machine for operating and monitoring dialysing devices is disclosed, including a holder pivotable about a holding axis and extending from the dialysis machine for handling of fluid to be processed inside that dialysis machine, the holder including a connector to connect the holder to a fluid coupler so that the fluid can flow between the fluid coupler and the dialysis machine, with the connection axis of the connector being transverse to the holder axis of the holder.

11 Claims, 6 Drawing Sheets

COMBINED HOLDER AND CONNECTOR FOR A DIALYSER

FIELD OF THE INVENTION the present invention relates to a combined holder and connector for a dialyser. More particularly, the present invention relates to such a holder which is intended for use in hemodialysis, hemodiafiltration or hemofiltration when using a dialysis machine such as the GAMBRO AK 100 and during use of a dialyser, a hemofilter or the like.

BACKGROUND OF THE INVENTION

A dialyser is generally used to clean the blood of patients who have a reduced kidney function or endstage renal disease ESRD. The dialyser principally consists of a semi-permeable membrane, on one side of which passes blood and on the other side of which passes a dialysis solution. By designing the composition of the dialysis solution in a specific manner, an exchange of electrolytes across the semi-permeable membrane and reconditioning of the blood can thus take place. A hemofilter is a dialyser in which a fraction of the blood, namely an ultrafiltrate, is separated, and replacement fluid is supplied directly to the blood.

The dialyser is operated and monitored by means of a dialysis machine, for example one having a construction as described in European Patent No. B1-278,100. Such a dialysis machine is sold by Gambro AB under the trademark GAMBRO AK 100.

Before using a dialyser, it must first be primed, i.e. filled with sterile physiological common salt solution whereby all the air in the dialyser is forced out and any remaining impurities are flushed out. This often occurs in a separate priming stage in a manner such that sterile priming solution is allowed to pass through the dialyser in the same manner as the blood is to later pass, while ordinarily normal dialysis solution is supplied to the dialyser on the other side of the membrane. The priming step preferably occurs with the dialyser upside down as compared to the treatment position, in order to be more certain of having forced all of the air out of the dialyser.

To this end, the above-mentioned dialysis machine GAMBRO AK 100, is provided with a holder for the dialyser which allows placement of the dialyser in two positions, namely, a priming position and a treatment position. This is normally effected by the holder gripping the dialyser around the middle, and by the holder being rotatable 180° about a horizontal axis.

The disadvantage with this procedure is that the priming stage has to be carried out manually, which, in turn, requires the personnel's time, which thus costs money. This manoeuvring of the dialyser between the two positions can also lead to tubes coming loose as a result of the human factor.

U.S. Pat. No. 4,191,351 describes a degassing means for a fluid flow transfer apparatus, such as a hemodialyser. It mainly refers to plate dialysers, and includes rotatable mounts and locking means, but no connector.

Furthermore, German Patent No. A1-3,642,671 discloses a fixed holder for a dialyser, which includes a quick release coupling for one of the connectors of the dialyser. The dialyser can be rotated 180 degrees around the axis of the connector to be primed in an inverted position.

However, the drawback of these prior art dialyser holders is that the dialyser is rotated around a symmetry axis comprising the coupling to the dialyser. Consequently, there is a substantial risk of leakage in the coupling. This would be detrimental to operation of the dialyser, since the pressure in the dialyser is normally below atmospheric pressure. Such leakage would let air into the dialysis compartment of the dialyser, leading to blockage of the membrane and a decrease in the efficiency of the dialyser. Moreover, there is a risk of introducing air into the patient's blood.

It is therefore an object of the present invention to provide a combined holder and connector for a dialyser which avoids the above-mentioned drawbacks of the prior art constructions.

It is another object of the present invention to provide a combined holder and connector for a dialyser in which the tube length is minimal, and therefore the risk of tubes becoming entangled and becoming loose is also minimal.

It is another object of the present invention to provide a holder for a dialyser which is motor-driven so that the dialyser can be placed in at least two positions, namely a priming position and a handling position, without intervention from personnel.

SUMMARY OF THE INVENTION

In accordance with the present invention these and other objects have now been realised by the invention of a combined holder and connector for a dialysis machine for operating and monitoring a dialysing device comprising a holding member pivotable about a holder axis and extending from the dialysis machine and adapted to handle a fluid to be processed by the dialysis machine, the holding member including a connection member for connecting the holding member to the fluid coupling member whereby the fluid can flow between the fluid coupling member and the dialysis machine, the connection member having a connection axis for the connection between the connection member and the fluid coupling member, the connection axis of the connecting member being transverse to the holder axis of the holding member.

In accordance with one embodiment of the combined holder and connector of the present invention, the fluid coupling member comprises a coupling nipple for the dialysing device.

In accordance with another embodiment of the combined holder and connector of the present invention, the dialysing device is selected from the group consisting of a dialyser, an ultrafilter, and a hemofilter.

In accordance with another embodiment of the combined holder and connector of the present invention, the holder axis is horizontal and the connector axis is perpendicular to the holder axis.

In accordance with a preferred embodiment of the combined holder and connector of the present invention, the holding member comprises a shaft extending horizontally from the dialysis machine. Preferably, the holding member is pivotable between a first angular position comprising a normal treatment position and a second angular position comprising a priming position, wherein the first and second angular positions are displaced 180° relative to each other. Preferably the holding member is also pivotable into a third angular position comprising a cleaning position.

In accordance with a preferred embodiment of the combined holder and connector of the present invention, the combined holder and connector includes a tube having a tube connector, the dialysis machine includes a dialysate outlet, and the tube is connected to the dialysate outlet whereby when the holding member is in the cleaning position, the tube connector is connected to the connecting member.

In accordance with another embodiment of the combined holder and connector of the present invention, motor means are included for pivotably driving the holding member.

In accordance with another embodiment of the combined holder and connector of the present invention, the connecting member includes guiding means for cooperatively engaging the connecting member with the fluid coupling member. In a preferred embodiment, the guiding means comprises a support member remote from the connecting means.

According to the present invention there is provided a combined holder and connector for a dialyser, a hemofilter or the like, which is arranged on a dialysis machine. The holder is preferably pivotable around a horizontal symmetry axis and comprises a connector for cooperating with a coupling arrangement of a dialyser for flowing a fluid to and/or from the dialyser. The symmetry axis of the connector differs from the symmetry axis of the holder.

According to one embodiment of the combined holder and connector of the present invention, the connector and coupling arrangement are intended for a dialysis solution and/or ultrafiltrate. According to a preferred embodiment, the symmetry axis of the connector is perpendicular to the horizontal symmetry axis.

In accordance with a preferred embodiment of the combined holder and connector of the present invention, the holder comprises a shaft extending horizontally out of the front of the dialysis machine. Preferably, the holder can be arranged for assuming two different angular positions, namely a normal treatment position and a priming position where the connector is displaced 180° relative to the treatment position. In addition, the holder can be arranged to assume a third angular position separate from the first two angular positions, which third position comprises a cleaning position. In that cleaning position, the connector is connected to a dialysate outlet from the dialysis machine by means of a tube and a connector.

In accordance with another preferred embodiment of the combined holder and connector, the holder is motor-driven between its various positions. In addition, it comprises a guiding arrangement for cooperation with the outer surface of the dialyser. Such a guiding arrangement may comprise a support member cooperating with the dialyser at a position remote from the holder and connector.

BRIEF DESCRIPTION OF THE DRAWINGS

The present invention can be more fully appreciated with reference to the following detailed description, in which.

DETAILED DESCRIPTION

Figure 1:
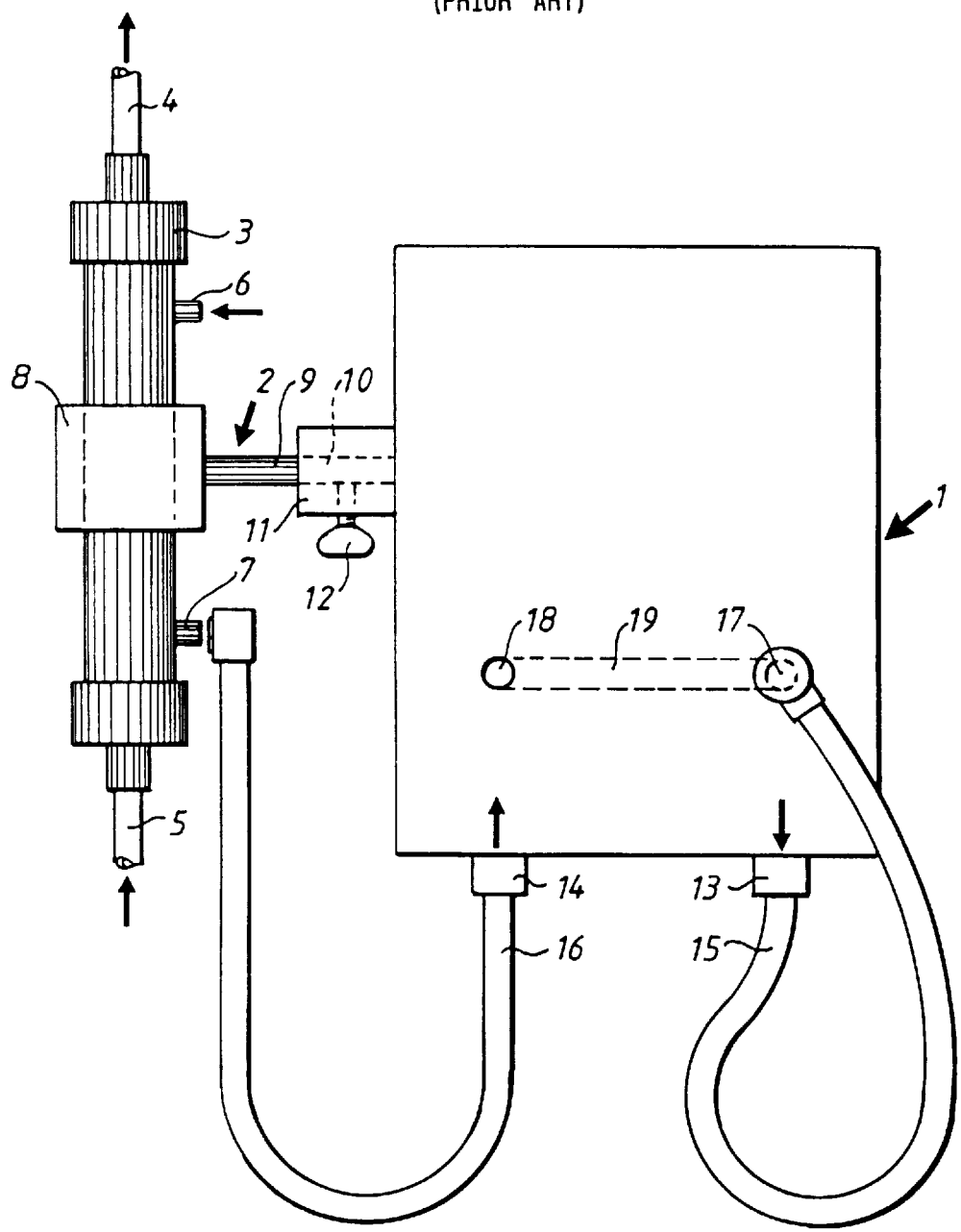
FIG. 1 is a schematic, front, elevational view of a dialyser holder in accordance with the prior art.

Referring to the Figures, in which like numerals refer to like elements thereof, FIG. 1 shows the lower left-hand portion of a prior art dialysis machine 1, e.g. of the GAMBRO AK 100 type. On its front face, the dialysis machine comprises a holder 2 for a dialyser 3, such as a hollow-fiber dialyser having a substantially circular cross-section. The interior space of the hollow fibers are connected by means of tubes 4 and 5, to the patient or, during priming, with a source of sterile priming solution, such as physiological common salt solution. The exterior space outside the hollow fibers is enclosed by a cylindrical tube. This exterior space is connected to coupling arrangements in the form of two nipples, 6 and 7, for connection to the circuit within the dialysis machine for dialysis solution.

The holder 2 comprises an engagement device 8 which cooperates with, and holds, the dialyser approximately at its middle. The engagement device 8 is provided with a rod 9 which is inserted into a horizontal hole 10 in a sleeve 11 in the side of the dialysis machine. The rod 9 is maintained within the hole 10 with the aid of a screw 12.

The dialysis machine 1 is provided with a drain 13 for dialysate solution and an inlet 14 for dialysate solution. The outlet 13 and the inlet 14 are provided with tubes, 15 and 16, which, in the stand-by position, are coupled to separate bypass couplings, 17, 18 and 19, positioned on the front of the dialysis machine. FIG. 1 shows the tube 15 from the outlet 13 coupled to the bypass coupling 17. The tube 16 is shown disconnected from the bypass coupling 18 and about to be attached to the lower nipple 7 of the dialyser, that lower nipple functioning as an outlet from the dialyser. The tube 15 is then disconnected from the coupling 17 and attached to the upper nipple 6 of the dialyser. Tubes 4 and 5 are coupled to the sterile priming solution. The dialyser is then ready for priming.

For priming, sterile physiological common salt solution is fed through the dialyser from below by means of the tube 5 and out through tube 4 so that all of the air is forced out from the spaces within the hollow fibers. At the same time, dialysate solution is supplied through inlet 6 and out through the outlet 7 in countercurrent flow.

When it has been established that all of the air has passed out through the outlet tube 4, the dialyser is turned 180° so that the nipple 7 will be uppermost and the nipple 6 lowermost. At the same time, the priming continues until the entire space above the hollow fibers is emptied of air. The tubes 4 and 5 are then coupled to the patient for treatment.

Figure 2:
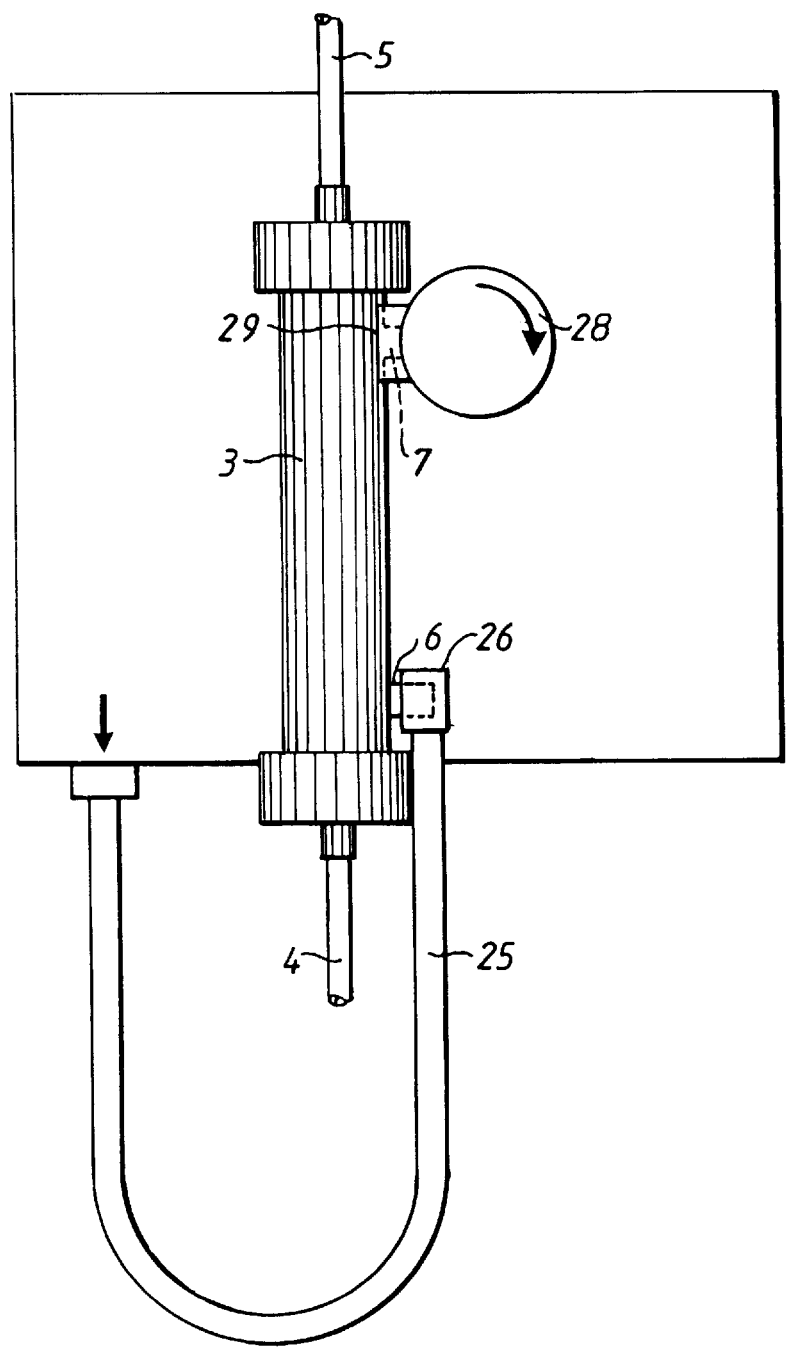
FIG. 2 is a schematic, front, elevational view of a dialyser holder according to the present invention.
Figure 3:
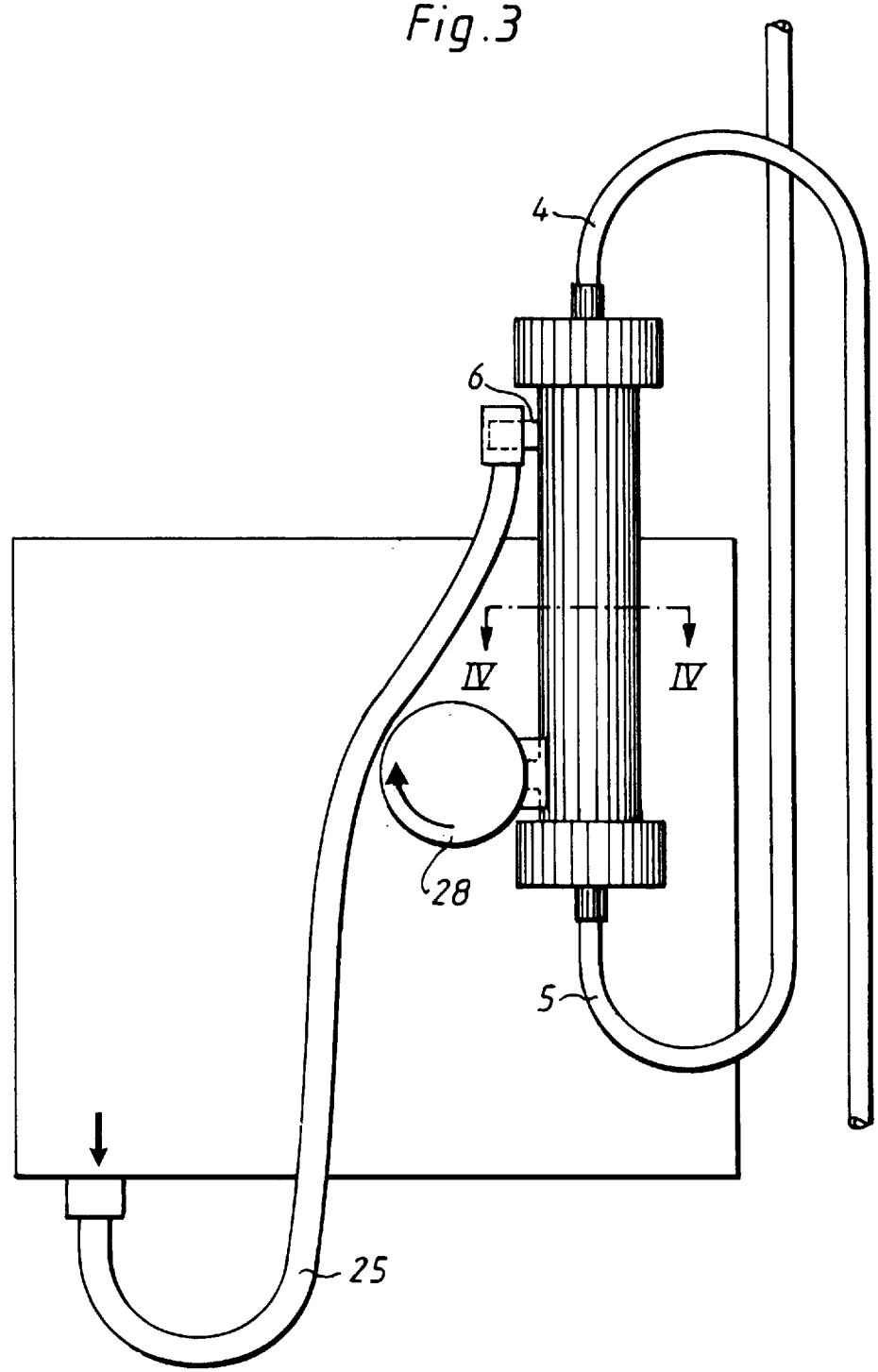
FIG. 3 is a schematic, front, elevational view of the dialyser holder of FIG. 2 with the dialyser in a priming position.
Figure 4:
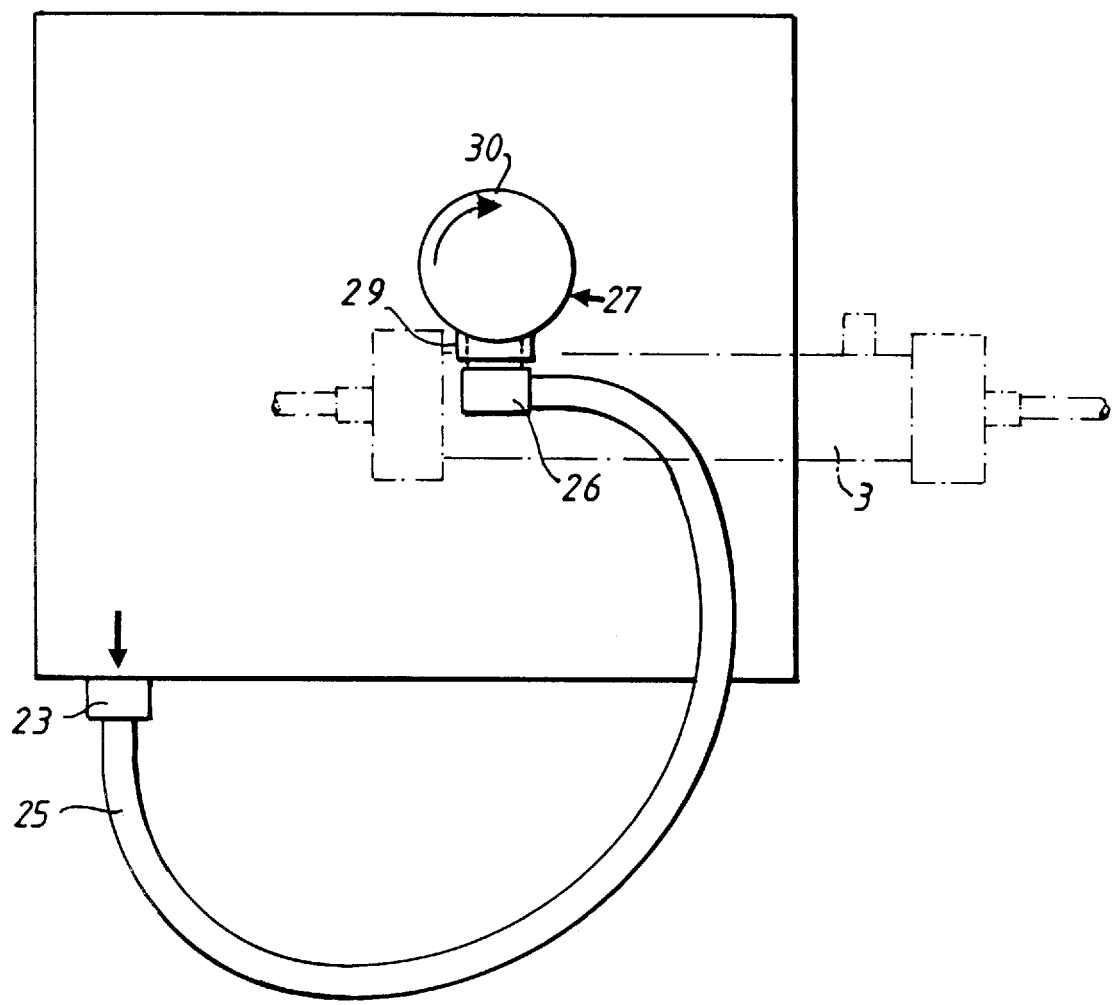
FIG. 4 is a schematic, front, elevational view of the dialyser holder of FIG. 2 with the dialysis machine in a cleaning position.

FIGS. 2, 3 and 4 show the same dialysis machine as in FIG. 1, but in this case modified in accordance with the present invention. Reference is first made to FIG. 4, which shows the machine in the stand-by position. The machine has been simplified according to the invention so that the inlet 14, the tube 16 and the bypass coupling 18 have been omitted.

The machine is provided with a dialysate outlet 23 and a dialysate tube 25, which has a dialysate connector 26 at its end. In the stand-by position, the dialysate connector is coupled to a connector arrangement 27, which will be explained in more detail below. In the stand-by position, the dialysate solution can thus circulate from the machine through the outlet 23 and the tube 25 to the connector 26 and back into the machine through the connector arrangement 27. No separate inner bypass conduit is therefore required.

The connector arrangement 27 consists of a shaft journal 28 or a cylindrical tube which extends horizontally outwardly from the front of the machine. In the lower side of the journal there is a connection 29 which leads to the connector 26.

The shaft journal 28 is rotatable into three different positions, as is shown in FIG. 4, FIG. 2 and FIG. 3, and as specifically indicated by arrow 30. In the position according to FIG. 4 the machine is in a stand-by position, which is detected by a sensor (not shown) within the machine. The sensor detects the three angular positions according to FIG. 4, FIG. 2 and FIG. 3. In the position according to FIG. 4 the dialysis machine can perform different programmed steps, such as rinsing, emptying, disinfection by means of heat or chemical means, etc.

From the position in FIG. 4, the shaft journal 28 can be rotated 90° clockwise to the position shown in FIG. 2, which constitutes the treatment position. In this position, the connector 26 is detached (manually or automatically) and a dialyser 3 is placed with its outlet nipple 7 (see FIG. 1) in the connector 29, which is now facing sideways, or towards the left in FIG. 2. The connector 26 is connected to the nipple 6 and the tubes 4 and 5 are connected as previously discussed.

The shaft journal 28 is then rotated an additional 180° clockwise to the priming position as shown in FIG. 3. Sterile priming solution passes through the tube 5, upwardly through the dialyser, and out through the tube 4, thereby taking with it air within the hollow fibers. At the same time, dialysis solution passes through tube 25 into the dialyser in the space outside the hollow fibers, as well as out through the shaft journal 28 and back to the machine.

After priming has been effected in this position, for a period of 10 minutes, for example, the shaft journal 28 is rotated 180° counterclockwise back to the position shown in FIG. 2, and priming is allowed to occur for an additional amount of time, whereupon the priming process is terminated and treatment can take place.

Figure 5:
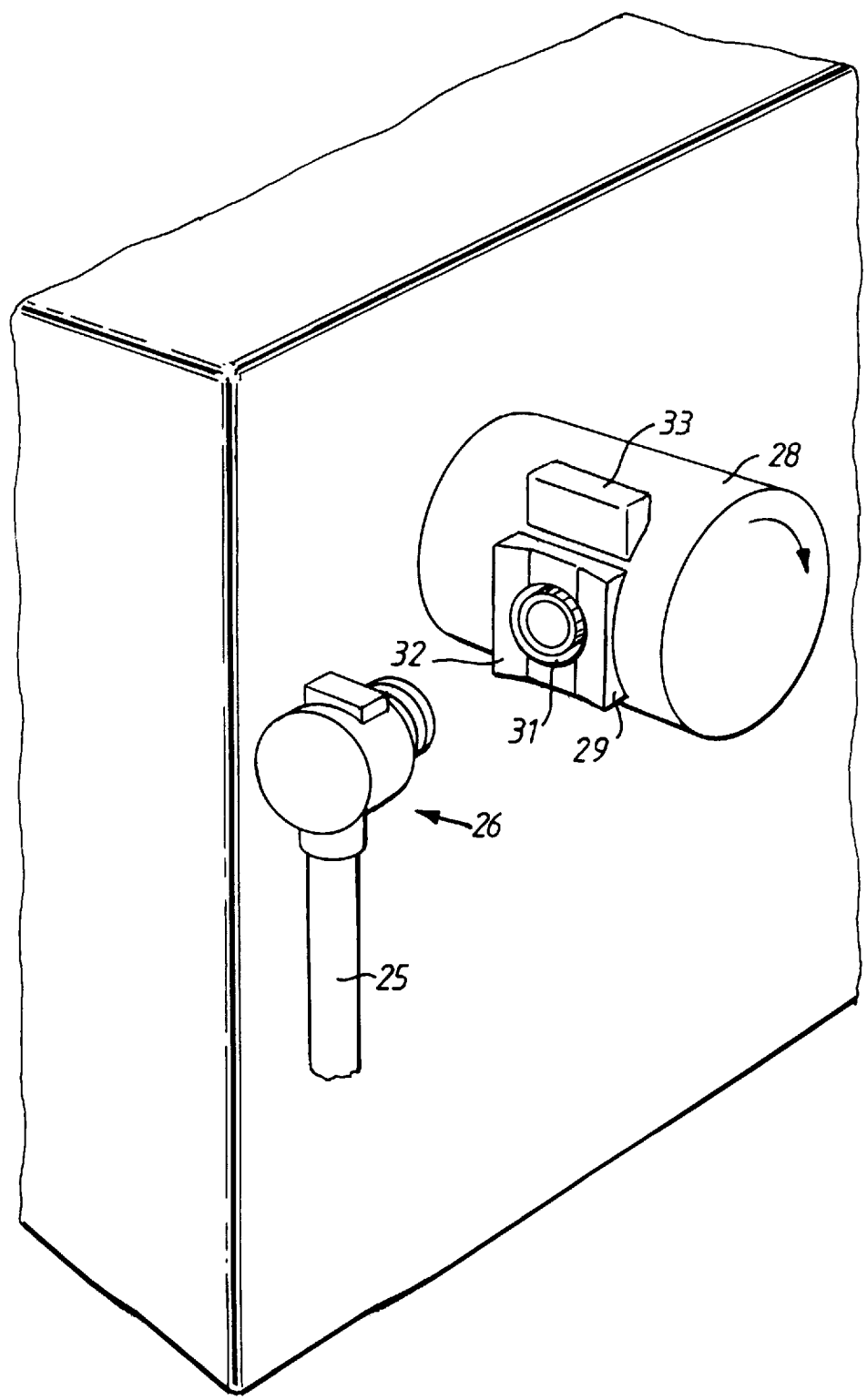
FIG. 5 is a front, side, perspective view of a dialyser holder in accordance with the present invention.

FIG. 5 shows the shaft journal 28 in perspective, and in a position which corresponds to FIG. 2. The connector 26 has hereby been detached from the connection 29, which is in a position facing towards the left and is ready for receiving a dialyser. The outlet nipple 7 of the dialyser is put into a hole 31 in the connector 29. The connector is provided with a guiding surface 32 which is formed so as to cooperate with the dialyser in order to guide same so that it remains vertical, as is described in more detail in connection with FIGS. 7 and 8.

The shaft journal 28 is additionally provided with a button 33 which is used for releasing the dialyser after use. When the nipple 7 of the dialyser is put into the hole 31, the button 33 springs upwardly and returns downwardly in order to engage around the nipple 7 and retain the dialyser safely in the holder 28.

The connector 26 can be detached with the help of the same button 33. Alternatively, the shaft journal 28 is provided with an arrangement which releases the connector 26 when the shaft journal moves from the position shown in FIG. 4 to the position shown in FIG. 2. This arrangement can furthermore lock the connector 26 in the position shown in FIG. 4 so that the connector cannot be detached by mistake.

In the same manner, there may be an inner lock arrangement in the shaft journal 28 which prevents the dialyser from being able to be detached in the position according to FIG. 3 or that the shaft journal can be rotated to the position according to FIG. 4 with the dialyser in place. In this way, it can be safely ensured that the dialysis machine operates in the intended manner in its different operating modes.

Figure 6:
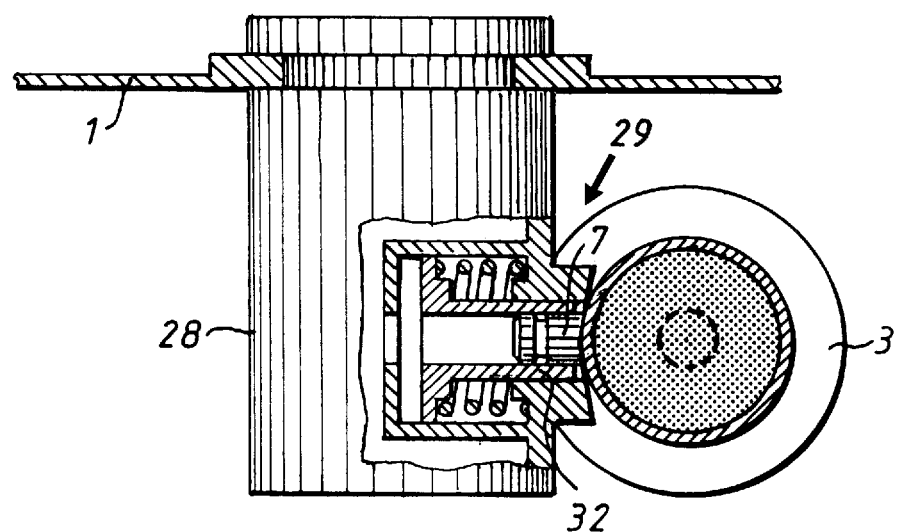
FIG. 6 is a top, elevational, partially sectional view of the dialyser holder according to FIG. 2 taken along lines VI—VI in FIG. 3.

FIG. 6 shows the dialysis machine according to FIG. 3, seen from above and taken along the line VI—VI in FIG. 3. In this case, the shaft journal 28 is shown from above, with a dialyser 3 of the hollow-fiber type, with a circular cross-section, located in the connector 29. As is clear from FIG. 6, the connector 29 comprises a spring-biased plate 32 which cooperates with the outer surface of the dialyser 3 around the nipple 7 so that the dialyser 3 cannot rotate around the nipple 7. In this manner, the dialyser 3 is maintained securely gripped by the connector 29. Moreover, it is assured that the dialyser nipple does not rotate in the connector 29, which could result in leakage problems.

Figure 7:
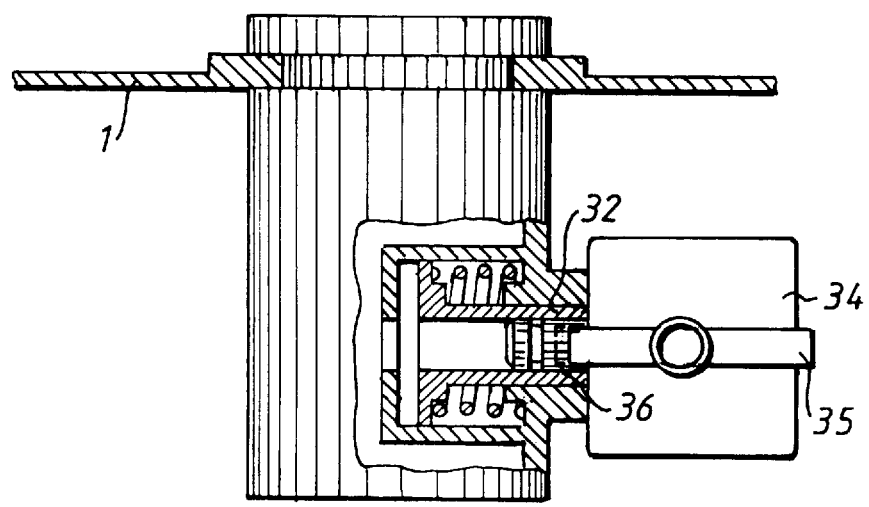
FIG. 7 is a top, elevational, partially sectional view of the dialyser holder shown in FIG. 2 connected with a different type of dialyser.

FIG. 7 shows a corresponding arrangement for a plate dialyser. The plate dialyser is provided with an encircling flange 35 which cooperates with a separate guide 36 in the plate 32.

The invention has been described above as a succession of steps from the position according to FIG. 4 to the position according to FIG. 2, and further to the position according to FIG. 3 for priming, as well as finally returning to the position according to FIG. 2 for treatment. Other sequences can of course be performed, for example from the position in FIG. 4 directly to the position according to FIG. 3 and thereafter to the position according to FIG. 2.

Additionally, it is also possible that other flow directions than those described above can be used. For example, the priming according to FIG. 3 can take place by a sterile priming solution passing through tube 5 upwardly through the dialyser to the tube 4, at the same time as dialysate solution passes from the shaft journal 28 and upwardly through the dialyser as well as out through tube 25, by the direction of the dialysate solution within the machine being reversed.

With hemofiltration, the hemofilter is only provided with one connection nipple 7, while the nipple 6 is not present. The dialysis machine can thus be provided with a connection (not shown) for the coupling 26, whereby attachment of the coupling 26 to this connector signals the dialysis machine that hemofiltration should be carried out. Priming occurs in that the sterile priming solution passes through the hollow fibers to the outer space of the hemofilter, by using an under-pressure by means of the holder 28. The operation is otherwise clear for a skilled person.

The dialyser normally has connector nipples, 6 and 7, but it is of course also possible to use other coupling arrangements on the dialyser, such as recesses, etc. The holder according to the present invention is coupled into the circuit for dialysis solution and/or ultrafiltrate.

It is also possible to let the shaft journal rotate forwardly and backwardly over a small angular range (+/−10°) during the priming stage in order to additionally facilitate priming.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A combined holder and connector for use in connection with a dialysis machine for operating and monitoring a dialyser comprising a pivotable holding member pivotably extendable from said dialysis machine about a pivot axis and adapted to handle a fluid to be processed by said dialysis machine, said pivotable holding member including a connection member for connecting said holding member to a fluid coupling member of said dialyser whereby said fluid can flow between said fluid coupling member and said dialysis machine, said connection member having a connection axis for said connection between said connection member and said fluid coupling member, said connection axis of said connecting member being transverse to said pivot axis of said holding member whereby upon connection of said connecting member with said fluid coupling member of said dialyser, said dialyser can be pivoted together with said holding member without any relative movement between said connecting member and said fluid coupling member of said dialyser.

2. The combined holder and connector of claim 1 wherein said fluid coupling member comprises a coupling nipple for said dialyser.

3. The combined holder and connector of claim 1 wherein said dialyser comprises an ultrafilter or a hemofilter.

4. The combined holder and connector of claim 1 wherein said pivot axis is horizontal and wherein said connector axis is perpendicular to said pivot axis.

5. The combined holder and connector of claim 1 wherein said holding member comprises a shaft extending horizontally from said dialysis machine.

6. The combined holder and connector of claim 5 wherein said holding member is pivotable between a first angular position comprising a normal treatment position and a second angular position comprising a priming position, wherein said first and second angular positions are displaced 180° relative to each other.

7. The combined holder and connector of claim 6 wherein said holding member is pivotable into a third angular position comprising a cleaning position.

8. The combined holder and connector of claim 7 including a tube having a tube connector, said dialysis machine including a dialysate outlet and said tube being connected to said dialysate outlet, whereby when said holding member is in said cleaning position said tube connector is connected to said connecting member.

9. The combined holder and connector of claim 1 including motor means for pivotably driving said holding member.

10. The combined holder and connector of claim 1 wherein said connecting member includes guiding means for cooperatively engaging said connecting member with said fluid coupling member.

11. The combined holder and connector of claim 10 wherein said guiding means comprises a support member remote from said connecting means.

* * * * *